United States Patent [19]

Schroeder et al.

[11] 4,215,052

[45] Jul. 29, 1980

[54] PRODUCTION OF LIQUID ORTHO-PHTHALIC ACID AND ITS CONVERSION TO HIGH PURITY PHTHALIC ANHYDRIDE

[75] Inventors: Hobe Schroeder, Warrenville; David A. Palmer, Naperville; George E. Kuhlmann, Naperville; Houssam M. Naim, Naperville; Nicholas C. Huie, Naperville, all of Ill.

[73] Assignee: Standard Oil Company (Indiana), Chicago, Ill.

[21] Appl. No.: 70,663

[22] Filed: Aug. 29, 1979

[51] Int. Cl.$^2$ .............................................. C07D 307/89
[52] U.S. Cl. .............................., 260/346.7; 260/346.4
[58] Field of Search ........................... 260/346.4, 346.7

[56] References Cited

U.S. PATENT DOCUMENTS

| | | | |
|---|---|---|---|
| 2,670,325 | 2/1954 | West et al. | 260/346.7 X |
| 3,402,184 | 9/1968 | Berthoux et al. | 260/346.4 |
| 3,484,458 | 12/1969 | Stein et al. | 260/346.4 |
| 4,165,324 | 8/1979 | Schroeder et al. | 260/346.7 |

*Primary Examiner*—Richard Raymond
*Attorney, Agent, or Firm*—Fred R. Ahlers; William T. McClain; William H. Magidson

[57] ABSTRACT

Phthalic anhydride of commercially acceptable quality can be produced continuously in yields of from about 80 up to about 83 mole percent (% of theoretical) through a combination of steps starting with the neat oxidation of liquid o-xylene with air in the presence of the catalysis provided by cobalt, manganese and bromine. Said oxidation is conducted in two steps wherein the first step is conducted under mild conditions and short residence time to provide a liquid effluent containing 8 to 40 weight percent o-phthalic acid and 6 to 30 weight percent o-xylene and the second step oxidizes such liquid effluent composition under more vigorous conditions including higher reaction temperature and longer residence time until substantially all of the o-xylene and precursors of o-phthalic acid have been converted to o-phthalic acid. Thereafter the second liquid oxidation effluent is subjected to simultaneous rapid dehydration and phthalic anhydride evaporation followed by contact of the resulting mixture of vapors first with a noble metal catalyst to remove bromine contamination and then with a reflux liquid in a fractionation system to remove water as part of a top fraction and provide a liquid partially purified anhydride as the bottom fraction which is heated with a catalytic amount of KOH to remove phthalide and finally the phthalide-free liquid partially purified anhydride is fractionated to obtain, in known manner, high purity phthalic anhydride product.

8 Claims, No Drawings

PRODUCTION OF LIQUID ORTHO-PHTHALIC ACID AND ITS CONVERSION TO HIGH PURITY PHTHALIC ANHYDRIDE

TECHNICAL FIELD

This invention relates to the continuous production of o-phthalic acid by the catalytic neat oxidation of liquid o-xylene with air to a liquid mixture containing from 85 up to 92 weight percent o-phthalic acid, from 3 to 7 weight percent water, from 0.1 to 1.0 weight percent phthalide, from 0.5 up to 8 weight percent benzoic acid, and lesser amounts of other oxygen-containing aromatic impurities followed by the continuous rapid conversion of o-phthalic acid to its anhydride under conditions which rapidly evaporate said anhydride and water and compounds boiling between the anhydride and water and removal of said vapor mixture which also entrains vapors of phthalide; the removal of bromine from said vapor mixture by contacting it with a noble metal catalyst; the continuous removal of water from said bromine-free vapor mixture by contacting it in a fractionating system with a reflux liquid which is inert to the components of said vapor mixture, boils at a temperature lower than said anhydride boils, and dissolves said anhydride at a temperature below the freezing point and up to the melting point of said anhydride; the continuous removal of phthalide by contacting said water and bromine-free mixture as a liquid with an alkali metal hydroxide; and the recovery of high purity phthalic anhydride by fractionation of said phthalide-free impure phthalic anhydride.

RELATED PATENT APPLICATIONS

U.S. Patent Application Ser. No. 50,159 filed June 20, 1979 describes the conduct of the two-step neat oxidation of liquid o-xylene; Ser. No. 22,431 filed Mar. 21, 1979, now abandoned, describes the rapid dehydration-evaporation applicable to the liquid effluent of said oxidation to remove a vapor mixture containing vapors of phthalic anhydride, water, benzoic acid, phthalide and other precursors of o-phthalic acid; Ser. No. 21,342, filed Mar. 19, 1979 describes removal of bromine from said vapor mixture by its contact with a noble metal catalyst; Ser. No. 969,879 describes the separation of water from such mixture of vapors by their contact in a fractionation system with an inert reflux liquid; and Ser. No. 898,930, now U.S. Pat. No. 4,165,324, describes the removal of phthalide from such bromine and water-free mixture with an alkali metal hydroxide.

STATE OF THE ART

The present invention comprises a combination of cooperating steps representing a novel and unique process for the production of o-phthalic acid, its conversion to its anhydride contaminated with precursor impurities and the recovery therefrom of high purity phthalic anhydride which meets the commercial specifications set therefor. Since the commercial anhydride product has long been produced by the air oxidation of a vapor phase of naphthalene or o-xylene in the presence of particles of solid catalyst containing vanadium, the art pertaining thereto and to the purification of impure phthalic anhydride obtain therefrom has not been found to be pertinent to the present inventive combination of cooperating steps except with respect to the final step of fractionation of partially purified phthalic anhydrides to obtain the anhydride as a high purity product. Moreover the two materially different modes of oxidation co-produce different types of impurities so that the purification steps between vapor phase oxidation and the final fractionation would not suggest routes or steps for partial purification of impure o-phthalic acid obtained by liquid phase oxidation.

However, British Patent Specification No. 856,245, published Dec. 14, 1960 is directed to a two-step oxidation wherein liquid o-xylene is oxidized neat (no extraneous solvent) in a mild first step in the presence of small amounts of cobalt or cobalt and bromine to incomplete oxidation product and the second step oxidizes the incomplete oxidation products in the substantial absence of o-xylene in the presence of more active catalysis provided by cobalt, manganese and bromine to a liquid impure phthalic anhydride product.

Such impure liquid phthalic anhydride is refluxed with water for 90 minutes to precipitate o-phthalic acid which is recovered by filtration and the filter-cake extracted with ether. The dried, ether extracted filter cake is said to be 98% pure o-phthalic acid. However the 2% impurities were not identified but probably did not contain catalyst metals. No processing scheme was presented for conversion of such 98% pure o-phthalic acid to phthalic anhydride of a commercially acceptable quality.

According to U.S. Pat. No. 3,402,184 o-xylene is oxidized with air in the presence of a liquid phase of an acetic acid solution containing cobalt, manganese and bromine ions as components of catalysis. The liquid effluent from such an oxidation contains phthalic anhydride dissolved in the acetic acid. According to the patent, the liquid effluent is diluted with water and the diluted effluent is heated to its boiling point temperature to hydrolyze the anhydride to o-phthalic acid which in part precipitates from the diluted acetic acid solution. The o-phthalic acid precipitate is recovered by means of effecting solid-liquid separation (e.g., filtration). While the separated o-phthalic acid precipitate is thermally converted back to phthalic anhydride, such anhydride had only a quality of partially purified anhydride and, as such, was not of commercially acceptable quality. Also a substantial proportion of the o-phthalic acid produced by hydrolysis of the anhydride dissolved in the liquid oxidation effluent remained dissolved in the dilute acetic acid solution. For the foregoing process to be commercially attractive such dissolved o-phthalic acid must be separated from the dilute acetic acid solution before or during recovery of acetic acid for its reuse in the o-xylene oxidation. Such second crop of o-phthalic acid or its anhydride derivative would be contaminated with catalyst metals.

Rather than starting with the oxidation process of either of the foregoing two patents, the present invention starts with the continuous two-step neat oxidation of liquid o-xylene described in copending patent application Ser. No. 50,159, filed June 20, 1979 before mentioned which produces a liquid mixture containing from 85 up to 92 weight percent o-phthalic acid rather than producing a liquid impure phthalic anhydride. It has been our experience with the continuous neat oxidation of liquid o-xylene at a temperature of from 150° C. up to 250° C. in the presence of the system of catalysis provided by at least cobalt and bromine that the oxidation of o-xylene diminishes in vigor when the liquid reaction mixture contains about 40 weight percent o-phthalic acid. At this point the liquid o-xylene is not miscible with the liquid o-phthalic acid phase containing the catalyst system and partial oxidation products. Such vigor-diminishing condition is readily observable by noting the change in volume ratio of o-xylene to water condensed from the exhaust mixture coming from the oxidation reaction. Such volume ratio changes from a normal range of 0.3 to 1 to 0.5:1 of the vigorous o-xylene oxidation through 1:1 and proceeds to as high as 2:1 as the oxidation vigor decreases and finally stops.

The two-step neat oxidation of liquid o-xylene comprising the first step of the present inventive process is conducted in a manner such that a mild first step produces a liquid mixture containing not more than 40, preferably not more than 25 weight percent o-phthalic acid and that in neither step is the o-phthalic acid permitted to be converted to phthalic anhydride. The difference in severities of the first and second oxidation steps can be accomplished, in general, by using low temperature in the first step and a combination of higher temperature and longer residence time in the second step or low temperature and catalyst concentration in the first step and higher temperature, higher catalyst concentration and longer residence time in the second step.

In TABLE I to follow, compositions typical of those produced by the two-step neat oxidation of liquid o-xylene with air are given. In said table the amounts of the components of the liquid reaction mixture flowing from the second oxidation step are in weight percent of said mixture.

TABLE I

| Reaction Effluent Compostions | | | | |
|---|---|---|---|---|
| Components: | | 2 | 3 | 4 |
| o-Phthalic Acid | 91.9 | 86 | 84.8 | 86.9 |
| o-Toluic Acid | 1.03 | 0.8 | 0.78 | 0.13 |
| Phthalide | 0.54 | 0.08 | 0.82 | 0.07 |
| 2-Carboxybenzaldehyde | 0.50 | 0 | 0.52 | 0.05 |
| High Boilers | 1.79 | 3.02 | 7.53 | 3.4 |
| Water | 3.45 | 4.87 | 4.5 | 3.4 |
| Benzoic Acid | 0.81 | 7.6 | 1.96 | 7.84 |

STATEMENT OF THE INVENTION

The present invention comprises the novel combination of cooperating sequential steps of (a) introducing continuously liquid o-xylene, air and an aqueous solution of catalyst components into a first stirred oxidation zone operated at a temperature of from 160° C. up to 225° C. and at a gauge pressure of from 21 up to 29 kg/cm$^2$ wherein the liquid reaction mixture contains from 0.2 up to 7 weight percent water wherein the ratio of aqueous solution of catalyst components provides from 0.25 up to 10 milligram atoms of cobalt, from 0.5 up to 5 milligram atoms of manganese and from 0.5 up to 40 milligram atoms of bromine per 1.0 gram mole of o-xylene; the ratio of air to xylene introduced provides from 2 to 15 volume percent oxygen in the spent air exiting the first oxidation zone and for a time sufficient to maintain a liquid reaction mixture containing from 8 up to 40 weight percent o-phthalic acid and from 6 up to 30 weight percent o-xylene; (b) introducing continuously the liquid reaction mixture produced in the first oxidation zone, air and additional catalyst components into the second stirred oxidation zone operated at a temperature of from 210° C. up to 230° C., a gauge pressure of from 26.7 up to 32 kg/cm$^2$ wherein the liquid reaction mixture in the second oxidation zone is maintained with a water content of from 1 up to 7 weight percent, wherein the additional catalyst components introduced provides a system of catalysis which comprises at least 1.0 milligram atom of cobalt per 1.0 gram mole of o-xylene charged to the first oxidation zone, and wherein the air to first oxidation effluent ratio is such that the spent air exiting the second zone contains from 5 up to 10 volume percent oxygen, for a residence time sufficient to provide a liquid reaction effluent containing from 85 up to 92 weight percent o-phthalic acid; (c) the liquid reaction effluent from the second stirred oxidation zone is continuously introduced into a combination dehydration-evaporation zone operated under conditions which rapidly dehydrate o-phthalic acid to phthalic anhydride and rapidly evaporate said anhydride and compounds boiling at a temperature between the boiling temperatures of said anhydride and water; (d) continuously introducing said vapor mixture into and through a bed of noble metal catalyst to remove bromine contamination from the vapor mixture; (e) continuously introducing said bromine-free vapor mixture which contains entrained phthalide into a fractionation system for contact with liquid reflux liquid immiscible with water and which has a boiling temperature below the boiling temperature of phthalic anhydride and is a liquid below the freezing temperature of said anhydride and is a solvent therefor wherein said fractionation system vapors of water and said reflux liquid are taken as a top fraction and a liquid impure phthalic anhydride is removed as a bottom fraction and wherein said top fraction is cooled to liquify water and the reflux liquid and is returned to the fractionation system; (f) continuously charging said impure phthalic anhydride bottom fraction and an aqueous solution containing at least 50 weight percent potassium hydroxide into a heating zone operated at a temperature of from 250° C. up to 350° C. and a residence time of from 2 to 8 hours whereby phthalide is removed; (g) continuously charging the phthalide-free impure phthalic anhydride to a second fractionation system wherefrom compounds boiling below phthalic anhydride are withdrawn as a first fraction, high purity phthalic anhydride is withdrawn as a second fraction and compounds boiling higher than said anhydride are withdrawn as a liquid bottom residue fraction.

SPECIFIC EMBODIMENTS

A. Two-Step Oxidation

TABLE II

| More desirable operating conditions for the two sequential oxidation steps are: | | |
|---|---|---|
| | A. First Step | B. Second Step |
| Operating Temperature, °C. | 160 to 205 | 210 to 227 |
| Operating Pressure, kg/cm$^2$ | 25 to 29 | 25 to 29 |
| Co Concentration, mga/gm xylene | 0.5 to 5.0 | 1.0 to 10 |
| o-Xylene Concentration, wt. % | 5 to 29 | — |
| o-Phthalic Acid Concentration, wt. % | 8 to 26 | — |
| Gram Atom Ratio Co:Mn:Br | 1:0.5 to 5:2.2 to 5.5 | — |
| Residence Time, min. | 40 to 80 | 120 to 210 |
| Water Concentration wt. % | 0.2 to 7 | 1 to 7 |

The preferred operating conditions for the two sequential oxidation steps are:

TABLE III

| | A. First Step | B. Second Step |
|---|---|---|
| Operating Temperature, °C. | 185 to 190 | 212 to 215 |
| Operating Pressure, kg/cm² | 28 to 29 | 28 to 29 |
| Co Concentration, mga/gm xylene | 0.8 to 1.0 | 1.3 to 1.5 |
| o-Xylene Concentration, wt. % | 6 to 10 | — |
| o-Phthalic Acid Concentration, wt. % | 24 to 28 | — |
| Gram Atom Ratio Co:Mn:Br | 1:0.5 to 2:2.5 to 4 | — |
| Residence Time, min. | 40 to 55 | 135 to 180 |
| Water Concentration, wt. % | 2 to 4 | 2 to 4 |

C. Dehydration and Evaporation

The recovery of a partially purified phthalic anhydride (PAN) from the liquid effluent containing, on a weight basis, from 85% up to 92% o-phthalic acid, from 1.0 up to 7% water, from 0.5 up to 8% benzoic acid, and lesser impurity amounts of oxygen-containing aromatic compounds boiling above and below the boiling temperature of PAN including precursors of o-phthalic acid as well as compounds containing cobalt, manganese and bromine derived from the catalysis used for the preparation of such effluent, is characterized by the continuous in situ dehydration of o-phthalic acid to PAN and flash evaporation of it from the liquid effluent leaving a fluid residue containing the materials boiling above the boiling temperature of PAN, and continuously removing the vapor fraction and the liquid residue fraction as separate streams from the site of such dehydration and flash evaporation.

Such rapid dehydration to and evaporation of partially purified PAN can be suitably effected by introducing the fluid oxidation product into a combination dehydration-evaporation zone maintained at a pressure in the range of from 760 mm Hg down to 40 mm Hg, preferably in the range of from 250 mm Hg down to 75 mm Hg, and at a temperature in the range of from 180° C. up to 250° C. and removing from such zone the separate vapor fraction stream and the liquid residue stream.

For efficient fluid flow out of the dehydration-evaporation zone, the fluid residue, i.e., a mixture containing materials boiling at a temperature above the boiling temperature of PAN, can contain from 10 up to 60 weight percent PAN as a viscosity-reducing flux. Loss of PAN to the residue will be from one up to four weight percent of the PAN equivalent of o-phthalic acid in the feed. Much of the residue's PAN can be extracted with water as o-phthalic acid.

The mixture of vapors withdrawn from the heating-vaporizing zone comprises water as the non-organic portion and the organic portion comprising mainly (81-99 wt%) PAN together with benzoic acid (up to 8 wt.%); the precursors (o-toluic acid, 2-carboxybenzaldehyde and phthalide) which amount in toto to from 1.13% up to 1.8% by weight; and the accompanying bromine-containing compounds in amounts of less than 1000 ppm.

Removing the fraction comprising the mixture of vapors and the fluid metals-containing bottoms fraction from the heating and vaporizing zone substantially as rapidly as such fractions are formed minimizes contact between liquid PAN and the metals-containing bottoms fraction. Such minimum contact is an essential critical feature of the present invention. We have found that moderate to relatively long contact between liquid PAN and said metals-containing residue fraction enhances decomposition of PAN thereby lowering its yield and adds, in some way, new colored or color-forming impurities which cannot be removed from PAN by any commercially feasible and economic process.

The liquid effluents from the various neat oxidations of liquid o-xylene are obtained therefrom at a temperature of from 150° C. up to 250° C. and at a pressure of from 17.6 kg/cm² up to 30 kg/cm². Since the foregoing step is conducted at a lower pressure of from one atmosphere (760 mm Hg) down to 0.05 atmosphere (40 mm Hg), sudden decompression of said liquid effluent to such lower pressure could cause solidification of the effluent unless it is maintained at a temperature at which the effluent remains a liquid. This can be readily accomplished by combining the effluent with additional liquid water at the effluent's pressure to increase the water content to 15 to 20 weight percent of the diluted effluent and maintaining its temperature at 200° C. to 220° C. and feeding such diluted effluent into the dehydration and evaporation zone. Alternatively, the liquid effluent can be used directly by combining it with a large volume of liquid residue (PAN and water depleted effluent).

D. Removal of Bromine

The bromine content of partially purified phthalic anhydride obtained from step (c) can be diminished to less than 3 ppm by weight based on the anhydride by contacting the vapors of such partially purified anhydride and water vapor with a particulated solid catalyst comprising from 0.01 up to 10 weight percent, preferably 0.1 to 1.0 weight percent, metallic palladium or platinum disposed on the surface of carbon or charcoal (hereafter Pd/C or Pt/C). Such carbon or charcoal is known as activated carbon. Suitably such activated carbon has a surface area to mass ratio of at least 100 and up to 3000 m²/g, and preferably from 500 to 2000 m²/g.

Such contact treatment is of short duration, merely passing the vapors of the partially purified phthalic anhydride through a short bed of such particulated catalyst will provide a sufficient contact time for the practice and the purposes of this invention.

It is indeed surprising that merely contacting the vapors of the partially purified phthalic anhydride and small amount of water vapor with the Pd/C or Pt/C catalyst in the absence of hydrogen can effect the debromination to a concentration of less than 3 ppm by weight of the anhydride.

The limit of the X-ray fluorescence detection analytical technique to detect bromine in a composition containing phthalic anhydride is 3 weight part of bromine per $1.0 \times 10^6$ (million) weight parts of the anhydride, i.e., 0.0003 wt.%. Thus "less than 3 ppm by weight of bromine based on the anhydride" means no detectable bromine.

We have discovered that the treatment of liquid partially purified PAN with hydrogen and Pd/C catalyst does not effectively cause debromination of the bromoaromatic impurity: ArBr, as might be expected according to the equation

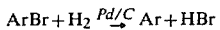 ArBr+H$_2$ $\xrightarrow{Pd/C}$ Ar+HBr

However, when water vapor is present, effective debromination of the aromatic impurity (ArBr) possibly occurs in the vapor state in the presence of Pd/C catalyst according to the equation

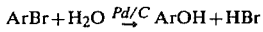 ArBr+H$_2$O $\xrightarrow{Pd/C}$ ArOH+HBr

Thus, the presence of a "small amount" of water with partially purified PAN would be a quantity of water at least equal to 0.25 times the weight percent of bromine present. Greater quantities of water, for example, up to 20 weight percent of the mixture of PAN and water can be contacted with the Pd/C catalyst without diminishing the debromination effectiveness.

The amount of catalyst useful in step (d) of this invention depends on the Pd or Pt content of the catalyst. The Pd/C or Pt/C particulated catalyst will provide a low pressure drop bed when the catalyst particles are of a size not smaller than 1.69 mm nor larger than 4.75 mm. That is, such particles will not pass through a sieve with 1.68 mm openings but will pass through a sieve with 4.76 mm openings. The catalyst bed need not consist of a single particle size but can comprise a mixture of particle sizes from 1.69 up to 4.75 mm. Such a bed of diverse particle sizes having a Pd or Pt content of from 0.01 up to 10 weight percent can be, with respect to the vapor mixture to pass therethrough, of from 10 to 1000 grams of catalyst per kilogram of the vapor mixture.

The temperature of the vapor mixture from step (c), that is from 180° up to 250° C., will provide an adequate catalyst bed temperature for the debromination according to this step (d) of the present invention.

To facilitate transfer of said vapor mixture obtained at a pressure of from 760 mm Hg down to 40 mm Hg to said catalyst bed, the vapor mixture is compressed to overcome the pressure drop caused by said bed, preferably such compressor should be 0.2 to 0.5 kg/cm$^2$ above said pressure drop.

E. Separation of PAN From Mixture of PAN and Water Vapors

The separation of phthalic anhydride from a vapor mixture containing 60 to 85 weight percent of said anhydride and 25 to 10 weight percent water vapor with the remainder comprising vapors of benzoic acid, o-toluic acid and materials boiling near or just above said anhydride withdrawn from the previous step involves contacting such vapor mixture in countercurrent flow with a reflux liquid at a temperature below the boiling point of phthalic anhydride to condense it and dissolve its condensate. Said separation is effected by exchange of heat from the vapor mixture to vaporize some of the reflux liquid. Its vapors and water vapor move upward in a rectification zone countercurrent to the flow of reflux liquid and form a vapor mixture enriched in water vapor and vapor of the reflux liquid but depleted in vapors of benzoic acid, toluic acid and aromatic compounds having boiling temperatures above that of water but below such acids. Such enrichment in water vapor and vapors of reflux liquid continues until the rising vapor mixture contains substantially only vapors of water and the reflux liquid. The mixture of substantially only vapors of water and reflux liquid is cooled to a temperature below the boiling temperature of water, thereby condensing both the reflux liquid and water. The water condensate separates from the reflux liquid's condensate. The water layer is discarded. The cool reflux liquid condensate layer is recycled to said rectification separation.

The reflux liquid moves from the rectification down through said contact with the feed vapor mixture to a stripping zone wherein the reflux liquid carrying phthalic anhydride condensate as dissolved liquid and/or solvent becomes enriched with respect thereto and with respect to benzoic and o-toluic acids and phthalide. The reflux liquid containing phthalic anhydride, benzoic acid, o-toluic acid and phthalide is heated to a temperature which vaporizes the reflux liquid but not phthalic anhydride but rather the heating leaves the anhydride as a liquid in which phthalide, benzoic acid and o-toluic acid become dissolved.

Such a concept for PAN separation requires as the reflux liquid a substantially pure single compound or a mixture of boiling point related compounds so that there is no component of the reflux liquid which will remain with and contaminate phthalic anhydride. The reflux liquid must be an inert solvent or absorbent for phthalic anhydride, benzoic acid, and o-toluic acid at low temperatures, e.g., below the anhydride's freezing point and up to its melting point, and miscible with said benzene carboxylic acids at higher temperatures between their melting and boiling point temperatures. The reflux liquid must be immiscible and unreactive with water to facilitate their separation for recycle of the reflux liquid and minimize its loss in the separated water condensate. The reflux liquid must have a vapor pressure higher than the vapor pressure of phthalic anhydride to be readily separable therefrom but sufficiently low to remain substantially liquid after contact with the hot, 180° to 235° C. feed, and move through the stripping zone. Lastly, the reflux liquid should not form an azeotrope with either one or all of phthalic anhydride, benzoic acid or o-toluic acid.

The most convenient use of such reflux liquid is in a combination of a rectification zone above a feed zone, a stripping zone below the feed zone, a zone for vaporizing the reflux liquid at a temperature above the melting point but below the boiling point temperatures of phthalic anhydride and transferring the reflux liquid vapors to contact the reflux liquid carrying in solution or by absorption phthalic anhydride, benzoic acid and o-toluic acid, and a zone to receive and cool the mixture of water and reflux liquid vapors to condense them for their separation and recycle of the reflux liquid condensate. Said combination of condensation zone, rectification zone, feed zone, stripping zone and reboiling zone define, of course, a fractionation system (e.g., fractionating tower).

Methylbenzoate is the preferred reflux liquid to use in the fractionation system for effectively removing water vapor from a mixture thereof with vapors of phthalic anhydride, benzoic acid, o-toluic acid and phthalide. Pseudocumene (1,2,4-trimethylbenzene) can also be used as such reflux liquid.

The amount of methylbenzoate reflux liquid used relative to the amount of water present in the feed can vary from 8 to 20 on a volume to volume basis. Typically from 0.7 up to 0.9 mole of methylbenzoate is refluxed per mole of vapor fed to the fractionation system. The amount of pseudocumene reflux liquid used is from 1.5 to 3.0 moles per mole of vapor fed to the fractionation system.

One example of such fractionation system is provided by a top recycle tray, a 15-tray column for rectification zone below the recycle tray, a feed tray below the rectification zone, and a 20-tray column as the stripping zone below the feed tray. Said trays have a 50%-85% separation efficiency. Both of said columns are vacuum jacketed as are the feed and recycle trays. An externally heated reboiler having a side outlet for liquid removal supplies heat for the stripping zone by vaporizing at least the reflux liquid flowing down the stripping zone into said reboiler. The reboiler is operated at a temperature of from 200° C. up to 250° C. and a pressure of from 0.19 up to 0.33 atmospheres; i.e., from 150 mm Hg up to 250 mm Hg.

As it will be appreciated by a chemical process design engineer, such fractionation system towers or columns can be any of the trayed or packed columns generally useful for fractionation.

Vapor from above the recycle tray is transferred through a heat-traced line to a condenser cooled to a temperature of from 25° up to 43° C. above a decanter from the side of which the top aqueous phase flows into a receiver and from the bottom of which the reflux liquid condensate returns through a reflux control valve and meter. A water cooled knockback condenser is in the vacuum line to minimize removal of low boiling compounds into the vacuum system. Pressure at the top of the rectification column can be maintained at 150 torr (0.2 atmosphere) by a control valve operated by a pneumatic controller and an absolute pressure transmitter.

F. Removal of Phthalide From PAN

The liquid mixture containing mainly phthalic anhydride (PAN) and impurity concentrations of benzoic acid, phthalide, o-toluic acid and 2-carboxybenzaldehyde, if any of the latter be present, is removed from the reboiler of the preceding step at a temperature of 200° C. up to 250° C., is held at that temperature or even heated under pressure up to 350° C. in the presence of a catalytic amount, from 1.0 up to 10 milligram moles per one gram mole of impure phthalic anhydride, of an alkali metal hydroxide having a molecular weight of at least 40 (e.g., molecular weight of 40, 56, 102 or 150). No distillation or solid-liquid separation is used in this step of phthalide removal. Rather only the foregoing heating in the presence of said alkali metal hydroxide causes the phthalide per se to disappear (i.e., no longer analytically detectable) from the impure PAN.

The duration of such heating of impure PAN in the presence of said alkali metal hydroxide varies with the concentration of the anhydride used and with the temperature of such heating. At equal concentrations and heating temperatures, the relative activities of the hydroxides are of the order of: Na<K<Rb<Cs. The phthalide removal activities of the different alkali metal hydroxides can be illustrated by their use at 275° C. for four hours at the concentration of 3.7 milligram mole per one gram mole of impure PAN containing 0.78 weight percent phthalide. After such treatment the samples of PAN were found by analysis to contain the residual concentrations of phthalide shown in TABLE IV to follow.

TABLE IV

| Hydroxide | Residual Phthalide, wt. % |
| --- | --- |
| LiOH | 0.37 |
| NaOH | 0.21 |
| KOH | 0.008 |
| RbOH | 0.007 |

TABLE IV-continued

| Hydroxide | Residual Phthalide, wt. % |
| --- | --- |
| CsOH | <0.001* |

*Limit of detectability is 10 ppm (0.001%) by weight.

Based on activity for phthalide removal as indicated in TABLE IV the preferred alkali metal hydroxides are those having a molecular weight of 56, 102 and 150; i.e., the hydroxides of potassium, rubidium and cesium. Based on economics, the use of potassium hydroxide is preferred because on a unit weight basis the hydroxides of rubidium and cesium costs are several hundred times that of potassium hydroxide. Therefore the most preferred alkali metal hydroxide is potassium hydroxide.

The variance of activity with temperature of the alkali metal hydroxides in this step can be illustrated by the use of 3.7 milligram moles per one gram mole of impure PAN and determining the half period (time for phthalide concentration to diminish by one-half) at different temperatures. Such half periods for said concentration of KOH are 10 minutes at 275° C., 103 minutes at 250° C. and (by extrapolation) more than ten days at 200° C.

The normal (760 mm Hg) boiling temperature of the impure PAN is about 275° C. Thus, this step which on the basis of operating time can be carried out suitably at a temperature from 250° C. up to 350° C. and preferably at a temperature of from 275° C. up to 300° C. Thus, the operating pressure is rather moderate and can be from one atmosphere (0 dg/cm² gauge pressure) with added inert gas up to 1.45 atmosphere (0.5 kg/cm² gauge pressure) at 300° C. with no added inert gas.

Impure PAN having a phthalide content of up to 2.0 weight percent can, upon treatment at 275° C. for four hours with 3.7 milligram moles KOH per one gram mole of impure PAN, decreases in phthalide content to less than 0.001 weight percent.

G. PAN Recovery by Fractionation

Following the foregoing step of phthalide removal the hot impure PAN is charged directly to a fractionation step conducted in known manner. Such fractionation of impure PAN containing benzoic acid, o-toluic acid and 2-carboxybenzaldehyde can be conducted at an operating pressure in the range of from 20 mm Hg up to 760 mm Hg absolute (i.e., from 0.026 up to 1.0 atmospheres). For continuous operation the fractionation system is conducted in two towers. The benzoic acid-containing or light ends fraction is removed as the top fraction of the first tower and PAN product fraction is removed as top fraction of the second tower. Operating at such pressures, the impurities, mainly benzoic and o-toluic acids, can be readily removed at reflux ratios of from 10:1.0 up to 50:1.0 as a first or light ends fraction amounting to about one percent by weight more than the sum of the impurities content. For example, when the phthalide-free impure PAN has a total impurity content of 2.6 weight percent, the first fraction taken will amount to 3.6 weight percent of the impure PAN charged. The reflux ratio will depend on the size of the light ends (benzoic acid-containing) impurity fraction to be taken relative to the feed. Minimum reflux ratio requirements are fixed by vapor-liquid equilibrium compositions and acceptable losses of PAN. As the reflux ratio is decreased, as evident to one skilled in the art, the PAN loss to the light ends fraction will increase.

The PAN product fraction can then be taken at a reflux ratio of from 1:1 to 5:1, preferably 1:1 to 2.5:1. There is left a residue (bottoms fraction of the second tower) containing residue from the alkali metal hydroxide reaction products and condensation products whose formation (e.g., product of the reaction of phthalide with PAN and/or benzoic or o-toluic acid) is catalyzed by the hydroxide. Such bottoms or residue fraction will amount to about 5 weight percent of the PAN charged and will contain 25 to 50% PAN so that the residue as a liquid has a viscosity such that it does not present a fluid transfer (gravity flow or forced flow) problem. The use of a viscosity lowering addition agent can decrease said loss of PAN to the bottom fraction.

The examples to follow is provided to enable those skilled in the art to understand and practice the present invention.

EXAMPLE 1

A. Two-Step Oxidation

The two-step oxidation is conducted under the conditions indicated in TABLE V to follow.

TABLE V

From Table III, ACM 77-257
Description: Xylene Feed - 93% Xylene, 7% Benzoic Acid

| A. | Step One Conditions | |
|---|---|---|
| | Pressure, kg/cm$^2$ G | 28.1 |
| | Temperature °C. | 165.6 |
| | O$_2$ in Exhaust, vol. % | 2.5 |
| | o-Xylene Feed, g/min. | 109.7 |
| | Cat. Comp./g. mole feed | |
| | Co, milligram atom | 1.51 |
| | Mn, milligram atom | 0.75 |
| | Br, milligram atom | 6.04 |
| | Air Rate, nl/min. | 214.3 |
| | Residence Time, min. | 54 |
| B. | Step Two Conditions | |
| | Pressure, kg/cm$^2$ G | 26.7 |
| | Temperature °C. | 212.8 |
| | O$_2$ in Exhaust, vol. % | 8.1 |
| | Feed, g/min. | 37.8 |
| | Cat. Comp./g. mole feed | |
| | Co, milligram atom | 2.05 |
| | Mn, milligram atom | 3.12 |
| | Br, milligram atom | 6.2 |
| | Air Rate, nl/min. | 61.4 |
| | Residence Time, min. | 138 |

The liquid effluent from the second oxidation step amounts to 170 grams per minute and contains 86.9 weight percent o-phthalic acid which is a yield of 87% of theory (87 mole %).

Samples of the liquid effluents from the first and second oxidation steps are found by analysis to contain the amounts of the components shown in TABLE VI to follow.

TABLE VI

EFFLUENTS' COMPOSITION

| Component, wt. % | Step One | Step Two |
|---|---|---|
| Phthalic Acid | 26.4 | 86.9 |
| Water | 5.2 | 3.4 |
| o-Xylene | 6.54 | Trace |
| Benzoic Acid | 8.38 | 7.84 |
| o-Toluic Acid | 31.0 | 0.13 |
| Phthalide | 7.51 | 0.07 |
| 2-CBA | 2.16 | 0.05 |
| High Boilers | 3.98 | 3.4 |

(C) Dehydration-Evaporation Step

For the o-phthalic acid dehydration to PAN and its flash evaporation in this example, the dehydration-evaporation vessel used is a thin film dehydration-evaporator having an evaporation surface of 16294 cm$^2$. Said evaporation surface is the surface of a horizontal cylinder rotatable in a tapered jacketed chamber. Said cylinder has on its surface four blades which have a 1.0 mm clearance from the inner jacket surface. The cylinder rotates at 1800 rpm for a tip speed of 10 m/sec. The vapor-liquid disengagement section is heated electrically to 180° C. The jacket is heated with circulating oil preheated to a temperature of 220° C. The jacket is co-extensive with the rotatable cylinder. A flanged glass residue receiver is located in the bottom of the vapor-liquid disengagement zone. A removable tubular vapor outlet containing a glass wool demister pad is connected to the feed inlet of a fractionation unit in which the reflux liquid is methylbenzoate.

An adjustable ram valve feeder is in the dehydrator-evaporator end of the fluid transfer line between the oxidation vessel wherein the catalytic neat oxidation of liquid o-xylene with air occurs at a gauge pressure of 28 kg/cm$^2$. Near the oxidation vessel end of the fluid transfer line there is a check valve to prevent back flow from the transfer line to the oxidation vessel. Between said check valve and said ram valve feeder there is an inlet in the transfer line to receive water under pressure.

The feed for the thin film evaporator comprises liquid oxidation effluent diluted with water to 18.5 weight percent and maintained under a gauge pressure of 10.2 kg/cm$^2$ and a temperature of 200° C. Said feed is introduced at a rate of 200 grams per minute into the thin film evaporator operated at a subatmospheric pressure of 210 to 230 mm Hg (0.276 to 0.30 atmosphere), at a feed section temperature of 230° C. and a liquid-vapor disengagement section temperature of 210° C. The residual liquid collected from the evaporator amounts to about 9.6 grams per minute and contains on a weight basis 38.3% PAN, 0.73% benzoic acid, 0.4% o-toluic acid, 0.05% 2-carboxybenzaldehyde, 0.42% phthalide, and 60.4% higher boiling compounds including organometallic compounds from the metal catalyst components. The feed and vapor mixture compositions are, on a weight basis, shown in TABLE VII to follow.

TABLE VII

COMPOSITION OF FEED TO AND VAPOR FROM EVAPORATOR

| Component, wt. % | Feed | Vapor |
|---|---|---|
| o-Phthalic Acid (Phthalic Anhydride) | 72.7 | 66.3 |
| o-Toluic Acid | 0.4 | 0.11 |
| 2-Carboxybenzaldehyde | 0.04 | 0.04 |
| Phthalide | 0.06 | 0.04 |
| Benzoic Acid | 6.56 | 6.85 |
| High Boiling Compounds* | 2.84 | 0 |
| Water | 18.0 | 26.7 |

*"High Boiling Compounds" include metal salts of organic acids.

The above vapor composition comprises 93.4% of the feed to the evaporator or 193.6 grams per minute of vapor mixture and can contain from 0.3 up to 0.8 weight percent organic bromides.

Step (D) Debromination

The 196.3 grams per minute of vapor mixture from step (c) at a temperature of 210° C. is taken by a blower and transferred through a bed of 790 grams of 1.69 up to 4.75 mm particles of palladium disposed on the surface of activated carbon having a palladium content of 0.5 weight percent. Such catalyst loading is 1.0 kg/hr of vapor mixture for 67.0 grams of catalyst.

Step (e) Separation of Water Vapor From PAN

Said 196.3 grams per minute of debrominated vapor mixture is fed to a fractionating column of the type before described but of larger volume and for separation of water vapor from PAN by the use of methylbenzoate as reflux liquid. The volumetric reflux ratio of methylbenzoate to water is 20:1.0. The column is operated at a subatmospheric pressure of 150 mm Hg (0.197 atmosphere) and a reboiler temperature of 215° C. The liquid product drawn from the reboiler (141.4 grams per minute) contains on a weight basis 90.8% PAN, 0.14% o-toluic acid, 0.05% 2-carboxybenzaldehyde, 0.06% phthalide, and 90% benzoic acid and has a bromine (organic bromide) content of less than 0.003%.

Step (f) Removal of Phthalide

The 141.4 gram per minute of liquid withdrawn from the foregoing step (e) is combined with 7.4 milligram moles of KOH per 1.0 gram mole of PAN and the mixture heated to a temperature of 275° C. for a four hour residence time. After such heating the liquid will be found by analysis to contain less than 0.001 weight percent phthalide and less than 0.0003% by weight bromine.

Step (g) Fractionation

The liquid from step (f) is charged to fractionation equipment operated at 0.13 atmosphere. A first (light ends) fraction is taken from the first tower top fraction at a reflux ratio of 50:1 in an amount of 26 grams per minute and contains all the benzoic acid, o-toluic acid and 2-carboxybenzaldehyde but only a small amount, 2.3%, of the PAN content of the material charged to fractionation. The PAN product fraction is taken as the second tower's top fraction at a reflux ratio of 2.5:1. Said product PAN fraction amounts to 96.7% of PAN content of the materials charged to fractionation. The bottoms fraction from the second tower, about one percent of the materials charged to the fractionation, contains about 50 weight percent PAN.

The product PAN fraction as a liquid will have an initial APHA color of 10 (Pt-Co scale) and an aged (ASTM Test Method D 1209-69) APHA Color of 40. The purity of the PAN product recovered from the foregoing process will be at least 99.8%.

The foregoing example of the present invention illustrates the dehydration-evaporation step by the use of liquid oxidation effluent water-diluted and maintained at a temperature of from 200° C. and a gauge pressure of about 10 kg/cm² fed to the then film dehydrator-evaporator operated at a sub-atmospheric pressure of from 0.276 and 0.3 atmosphere and a temperature of from 210° C. up to 230° C. with intermittent feed thereto. For continuous feed of the liquid effluent of neat o-xylene oxidation which can be at a temperature as high as 240° C. and a gauge pressure of 30 kg/cm² there is suitably at least one step of decompression to a gauge pressure in the range of from 5 to 12 kg/cm² when the liquid feed enters the dehydration-evaporation zone operated at a sub-atmospheric pressure of 40 to 250 mm Hg. Such decompression can be conducted through a pressure reducer which discharges the decompressed liquid below the surface of the liquid contents in a surge drum. Or the step of decompression can be accomplished by a means analogous to the ram valve feeder used in the foregoing examples. Such decompression is useful to avoid the sudden formation of solids and likely attendant plugging of the fluid transfer apparatus elements during decompression of the feed from the gauge pressures of 25 to 30 kg/cm² down to 40 to 200 mm Hg. Partial decompression for such purpose can be accompanied by water dilution of the liquid oxidation effluent when it contains less than 15 weight percent, e.g., from 3 to 15 weight percent water. Such dilution can be done by the addition of high pressure steam to the liquid effluent before its decompression to also avoid solidification of the decompressed feed. Dilution for such purposes can be to a water content up to 25, preferably a water content of 17 to 25 weight percent. Such amounts of water in the feed which evaporates with PAN acts to sweep it from the dehydration-evaporation step.

Another mode of practice of the dehydration-evaporation step of the present invention comprises the following procedural steps conducted in the manner and under the conditions described which involve a different concept for decompressing the oxidation reaction effluent.

The flow system used in the following illustrative example has been specially devised to decompress the fluid reaction effluent from the neat catalytic oxidation of liquid o-xylene with air. It will be appreciated that decompression of such fluid effluents from a gauge pressure of from 17 up to 28 kg/cm² (absolute pressure of from 18 up to 29 kg/cm²) down to a pressure of from 760 down to 40 mm Hg (absolute pressure of from 1.03 down to 0.054 kg/cm²), preferably 250 down to 100 mm Hg, would be accompanied by instantaneous evaporation and resultant precipitation of solids. Such instantaneous precipitation of solids would plug the inlet to the combination dehydration-evaporation zone because there is not sufficient liquid held therein to effectively prevent such solids precipitation upon injection of the fluid effluent below the liquid in said zone. The concept applied in solving said problem associated with the substantial decompression of the fluid effluent feed is to absorb the pressure drop energy by momentum transfer to a circulating liquid.

It will also be appreciated that the heat necessary to dehydrate o-phthalic acid in the oxidation effluent and evaporate its anhydride is not available in the fluid effluent going to the dehydration-evaporation zone. Hence additional heat must be supplied to said zone but must be done in such a manner so that the residence time in said zone and such heat addition do not cause decomposition and added discoloration of the phthalic acid anhydride product. By only dehydrating about 97 to 98% of the o-phthalic acid (PA) to its anhydride (PAN) in said combination zone there is left a rather small amount of fluid containing catalyst component. Such fluid can be rapidly circulated from said combination zone through an indirect heat exchange zone which provides the additional heat and then back into the combination zone. Such circulation for heat addition and retention of a small amount of fluid in a sump to supply such circulation can be accomplished in a total residence time of from 1.0 to 2.0 minutes, a adequately short residence time to avoid the decomposition and added discoloration.

The foregoing concept of absorption of pressure drop energy by momentum transfer can be practiced by injecting the pressurized fluid reaction effluent into the fluid circulating from the combination zone through an external heat exchange zone back to the combination zone.

EXAMPLE 2

Oxidation Steps (a) and (b)

The two-step oxidation of this example is conducted under the conditions indicated in TABLE VIII to follow.

TABLE VIII

| A. | Step One Conditions | |
|---|---|---|
| | Pressure, kg/cm$^2$ G | 28.1 |
| | Temperature °C. | 165.6 |
| | O$_2$ in Exhaust, vol.% | 3.5 |
| | o-Xylene Feed, kg/min. | 11.28 |
| | Cat. Comp./g. mole feed | |
| | Co, milligram atom | 1.44 |
| | Mn, milligram atom | 0.72 |
| | Br, milligram atom | 5.76 |
| | Air Rate, nl/gram mole xylene | 206 |
| | Residence Time, min. | 54 |
| B. | Step Two Conditions | |
| | Pressure, kg/cm$^2$ G | 28.1 |
| | Temperature °C. | 212.8 |
| | O$_2$ in Exhaust, vol.% | 10.0 |
| | Feed, kg/min. | 3.2 |
| | Cat. Comp./g. mole feed | |
| | Co, milligram atom | 2.25 |
| | Mn, milligram atom | 4.24 |
| | Br, milligram atom | 10.2 |
| | Air Rate, nl/kg feed | 2160 |
| | Reaction Time, min. | 165 |

The liquid effluent from the second oxidation step amounts to 1232 kg/hr and contains 86 weight percent o-phthalic acid which is a yield of 86.5% of theory (86.5 mole %).

Samples of the liquid effluents from the first and second oxidations are found by analysis to contain the amounts of the components shown in TABLE IX to follow.

TABLE IX

EFFLUENTS' COMPOSITION

| | Step | |
|---|---|---|
| Component, wt. % | One | Two |
| Phthalic Acid | 22.96 | 86.0 |
| Water | 6.1 | 6.6 |
| o-Xylene | 10.6 | 0.01 |
| Benzoic Acid | 0.56 | 0.58 |
| o-Toluic Acid | 38.03 | 0.94 |
| Phthalide | 6.64 | 0.65 |
| 2-CBA | 1.46 | 0.14 |
| Tolualdehyde | 2.53 | 0.02 |
| High Boiler | 2.46 | 1.7 |
| Accountability | 91.6% | 96.9% |

(c) Dehydration-Evaporation

In this example 1232 kg/hr of fluid oxidation effluent ("F.O.E.") produced by the continuous 2-step catalytic neat oxidation of liquid o-xylene is decompressed from 28.1 kg/cm$^2$ absolute pressure and a temperature of 213° C. by injecting such effluent into 13,445 kg/hr of circulating ("cycle") fluid which is most (about 99%) of the concentrate produced in the combination dehydration-evaporation zone. The smaller part (0.9 to 1.0%) of the concentrate, here 134.5 kg/hr, is withdrawn and mixed with 8 kg/hr of steam at a temperature of 160° C. and an absolute pressure of 5.98 kg/cm$^2$. Such mixture is fed to a stirred film evaporation zone operated at a temperature of 227° C. and an absolute pressure of 0.246 kg/cm$^2$. From the stirred film evaporation zone there are withdrawn 78.8 kg/hr of residue and 63.7 kg/hr of vapor mixture containing 76.3% phthalic acid anhydride (PAN). Said vapor mixture is fed into the vapor space above the combination dehydration-evaporation zone.

By injecting the 1232 kg/hr of fluid oxidation effluent at a temperature of 214° C. and an absolute pressure of 28.1 kg/cm$^2$ into the 13445 kg/cm$^2$ circulating ("cycle") liquid at a temperature of 202° C. and an absolute pressure of 0.246 kg/cm$^2$ there is produced a composite feed ("Feed") for the combination dehydration-evaporation zone amounting to 14677 kg/hr at a temperature of 199° C. and an absolute pressure of 0.492 kg/cm$^2$. Said feed is heated by indirect heat exchange to a temperature of 218° C. and thereafter flows into the combination zone operated at an absolute pressure of 0.246 kg/cm$^2$. Such operation of the combination zone results in the production of 1142.4 kg/hr of a mixture of vapors and gases containing 80.2 weight percent PAN. Such mixed vapors are combined with the vapors drawn from the wiped film evaporator. The combined mixtures of vapors and gases comprise the "Crude PAN" vapor product to be fed to the subsequent step of separation of PAN from water vapor according to the present illustration of this invention.

The amount (13,445 kg/hr) of "cycle" liquid might appear to violate the previous caution with respect to long residence exposure to dehydration-evaporation conditions. However, the low volume of such "cycle" liquid held in the combination zone and the high recycle rate of such "cycle" liquid result under the foregoing conditions of a rather low, 1.3 minutes, residence time in said zone as well as in the reheating (indirect heat exchange) zone.

The compositions of the foregoing streams of fluids and mixtures of vapors are shown in TABLE X to follow.

TABLE X

FLUID STREAMS COMPONENTS, WEIGHT PERCENT

| | Dehydration-Evaporation Zone | | |
|---|---|---|---|
| Component | "F.O.E." | "Cycle" | Feed |
| PA | 86 | | 7.2 |
| PAN | | 50.4 | 46.2 |
| Benzoic Acid | 0.58 | 0.48 | 0.49 |
| o-Toluic Acid | 0.94 | 0.63 | 0.66 |
| Phthalide | 0.65 | 0.42 | 0.44 |
| High Boilers | 1.7 | 36.9 | 33.94 |
| 2-Carboxybenzaldehyde | 0.14 | 0.11 | 0.11 |
| Co & Mn as Metals | 0.32 | 6.95 | 6.38 |
| Bromine | 0.38 | 0.42 | 3.8 |
| Water | 6.6 | 0 | 0.55 |

| | Film Evaporator | | | Crude PAN |
|---|---|---|---|---|
| Component | Feed | Vapor | Residue | Product |
| PAN | 50.4 | 79.8 | 21.5 | 80.17 |
| Benzoic Acid | 0.48 | 0.91 | 0.09 | 0.62 |
| o-Toluic Acid | 0.63 | 1.26 | 0 | 1.0 |
| Phthalide | 0.42 | 0.85 | 0.04 | 0.69 |
| High Boilers | 36.9 | 0 | 62.9 | 0 |
| 2-Carboxy-benzaldehyde | | 0.22 | | 0.17 |
| Co & Mn as Metals | 6.95 | 0 | 11.8 | 0 |
| Bromine | 4.12 | 4.35 | 3.55 | 0.042 |
| Water | | 12.56 | 0 | 16.9 |

Step (d) Debromination

The foregoing 1206.3 kg/hr of Crude PAN product vapors having 0.042 weight percent bromine and a temperature of 216° C. at a subatmospheric pressure of 0.24 atmosphere is heated to 250° C. by indirect heat exchange and compressed to 0.75 atmosphere for transport through a Pd/C catalyst bed comprising particles of from 1.69 up to 4.75 mm and having a palladium content of 0.42 weight percent, and maintained at a temperature of 250° C. at a catalyst loading of 50 grams of catalyst per 1.0 kg/hr of vapor mixture. The vapor mixture exiting said bed is transferred to step (e).

Step (e) Separation of Water Vapor From PAN

The 1206.3 kg/hr of "Crude PAN Product" mixture of gases and vapors at a temperature of 227° C. and absolute pressure of 0.246 kg/cm$^2$ (0.24 atmosphere) flows through a condenser and is cooled to a temperature of from 132° to 135° C. At said temperatures there condenses about 90% of the phthalic anhydride with a portion of each of benzoic acid, o-toluic acid, phthalide, higher boiling compounds and o-xylene if any be present. The condensate amounts to 937.2 kg/hr and is further processed in the next step. The uncondensed materials at 132°-135° C. comprise gases, the water vapor, the uncondensed PAN (10%), and the other aromatic derivatives present amounting to 278.94 kg/hr are fed to a tower having seven sieve trays and operated at a subatmospheric pressure of 0.13 atmosphere. The reflux liquid fed to the upper portion of said tower (i.e., above the top plate) is pseudocumene in an amount of 453.7 kg/hr and is at a temperature of 49° C. The gas-vapor mixture feed (278.94 kg/hr) enters the tower between the third and fourth trays from the bottom. The pseudocumene-water vapor mixture flows from the top of the tower to a condenser cooled to 49° C. The collected condensate forms a top pseudocumene layer which is recycled to the tower as reflux liquid and a bottom water layer, 145.43 kg/hr, which is drawn off and discarded. The materials flowing down the tower become enriched with respect to PAN as pseudocumene is vaporized therefrom by heat supplied by the tower's boiler. There is no significant concentration of pseudocumene in the liquid on the bottom tray at a temperature of 210° to 212° C. so that the liquid therefrom (mainly PAN with the parts of benzoic acid, o-toluic acid, or phthalide not first condensed at 132° to 135° C.) can be drawn off, about 128.5 kg/hr for further processing in the next step. Liquid of the composition on the first tray is heated in the boiler to a temperature of about 212° to 215° C. and recycled to the tower between the first and second trays.

(f) Removal of Phthalide

The 937.25 kg/hr of condensate at 132° to 135° C. and the 962.3 kg/hr of the 210° to 212° C. water and pseudocumene-free liquid bottoms from the water separation tower in step (e) are combined (combined liquids have a phthalide concentration of 0.69 weight percent) in a vessel operated at 0.24 atmospheric pressure and a temperature of 274° C. with 0.09 weight percent potassium hydroxide dissolved in water as a 50 weight percent KOH solution. The resulting mixture has a residence time of four hours at 274° C. temperature and subatmospheric pressure of 0.24 atmosphere.

(g) Fractionation

Liquid from the foregoing phthalide-removal step is removed at 1000 kg/hr and feed to a first rectification tower operated under a subatmospheric pressure at the top of 0.16 atmosphere. A low boiling fraction at a temperature of 197° C. and a reflux ratio of 50:1 is removed at 32.51 kg/hr. Said low boiling fraction contains benzoic and o-toluic acids and PAN, the latter in a concentration of 8 weight percent. The liquid residue at a temperature of 222° C. from the first rectification tower is pumped at 969.38 kg/hr into a second rectification tower operated at a top subatmospheric pressure of 0.13 atmosphere. A PAN product fraction at 961.7 kg/hr is taken at a 2:1 reflux ratio and a temperature of 204.4° C. The liquid residue from this second rectification amounts to 5.06 kg/hr and contains 50 weight percent PAN.

The recovered PAN product has a purity of 99.9 weight percent, an initial color as a liquid of 5 to 10 on the APHA color (Pt-Co) scale and an aged liquid color (ASTM Test D-1209-69) of 20 on said APHA scale. The recovered PAN product amounts to 98 weight percent of the PAN charged to the dehydration-evaporation step and has less than 0.0003% bromine.

The invention as claimed is:

1. A process for the preparation of liquid o-phthalic acid from liquid o-xylene, the conversion of said o-phthalic acid to impure phthalic anhydride, the purification of said anhydride, and the recovery of it as a high purity product by the cooperating sequential steps of:
   (a) the continuous neat oxidation of liquid o-xylene with air in a stirred oxidation zone operated at a temperature of from 160° C. up to 200° C. and a gauge pressure of from 21 up to 29 kg/cm$^2$ in the presence of catalysis provided by cobalt, manganese and bromine in the amounts based on one gram mole of o-xylene of from 0.25 up to 10 milligram atoms of cobalt, from 0.5 up to 5 milligram atoms of manganese and from 0.5 up to 40 milligram atoms of bromine and in the presence of from 0.2 up to 7 weight percent water in the reaction medium, with a ratio of air to xylene fed to provide 2 to 15 volume percent oxygen in the spent air exiting from the oxidation zone at a residence time sufficient to maintain a liquid reaction medium mixture containing from 8 to 40 weight percent o-phthalic acid and from 6 up to 30 weight percent o-xylene;
   (b) the continuous introduction of said liquid reaction medium mixture and air into a second stirred oxidation zone operated at a temperature of from 210° C. up to 230° C. and a gauge pressure of from 26.7 up to 32 kg/cm$^2$ in the presence of from 1 up to 7 weight percent water in the reaction medium with a ratio of air to said liquid reaction medium to provide from 5 up to 10 volume percent oxygen in the spent air exiting the second oxidation zone and in the presence of additional catalyst components which provides at least one additional milligram atom of cobalt per 1.0 gram mole of xylene charged to the first oxidation zone for a residence time sufficient to provide a liquid reaction effluent containing from 85 up to 92 weight percent o-phthalic acid in addition to liquid water and impurity amounts of benzoic acid, o-toluic acid, 2-carboxybenzaldehyde, phthalide, and higher boiling compounds including bromine-containing compounds;

(c) the continuous introduction of the liquid reaction effluent from the second oxidation zone into a combination dehydration-evaporation zone wherein o-phthalic acid is rapidly dehydrated to its anhydride and rapidly evaporated to a mixture of phthalic anhydride water, benzoic acid, o-toluic acid, 2-benzaldehyde and bromine containing compound vapors together with entrained phthalide vapors;

(d) the continuous introduction of said mixture of vapors into and through a bed of particles containing a noble metal whereby bromine contamination is removed;

(e) the continuous introduction of said mixture of vapors into a fractionation system whose reflux liquid is inert to the components in said vapor mixture, boils at a temperature below the boiling temperature of phthalic anhydride which is a liquid at the freezing point temperature of said anhydride and dissolves it at a temperature between its freezing and melting temperatures wherein liquid water is removed as one fraction and liquid partially purified phthalic anhydride is removed as a second fraction;

(f) the continuous introduction of said liquid partially purified phthalic anhydride and potassium hydroxide in an amount thereof of from 1.0 up to 10 milligram moles per 1.0 gram mole of phthalic anhydride into a heating zone operated at a temperature of from 250° C. up to a temperature of 350° C. for a residence time of from 2 up to 8 hours whereby a substantially phthalide-free liquid mixture forms; and (g) the continuous introduction of said phthalide-free liquid mixture into a second fractionation system wherefrom compounds boiling below the boiling point temperature of phthalic anhydride are removed as a first fraction, phthalic anhydride product is removed as a second fraction and compounds boiling higher than phthalic anhydride are removed as a liquid residue fraction.

2. The process of claim 1 wherein the first oxidation zone of step (a) is operated at a temperature of from 180° up to 190° C. and a gauge pressure of from 28 to 29 kg/cm$^2$ with a cobalt concentration of from 0.8 to 1.0 milligram atoms per 1.0 gram mole of o-xylene, a gram atom ratio of cobalt to manganese to bromine of 1:0.8 to 2:2.5 to 4, a water concentration of from 2 to 4 weight percent, an o-xylene concentration of from 6 to 10 weight percent and an o-phthalic acid concentration of from 24 up to 28 weight percent at a residence time of 30 to 40 minutes; and wherein the second oxidation zone of step (b) is operated at a temperature of from 212° C. up to 215° C., a gauge pressure of from 28 to 29 kg/cm$^2$, a water concentration of from 2 to 4 weight percent, a cobalt concentration of from 1.3 up to 1.5 milligram atom per 1.0 gram mole of xylene charged to the first oxidation zone, and with a residence time of from 135 up to 180 minutes.

3. The process of claim 2 wherein each of steps (c) through (g) is conducted continuously under a gauge pressure of from one atmosphere down to 0.05 atmosphere.

4. The process of claim 3 wherein the dehydration-evaporation of step (c) is conducted first to dehydrate 97 to 98 percent of o-phthalic acid to its anhydride, and then to dehydrate the remainder of said acid to its anhydride with the injection of steam into the dehydration mixture and the two-vapor products therefrom are combined and fed to step (d).

5. The process of claim 4 wherein phthalic anhydride is condensed from the combined vapor mixtures at a temperature of 130° to 135° C. and the uncondensed vapors are contacted in step (d) liquid with pseudocumene as the reflux liquid in an amount of from 1.5 up to 3.0 moles per 1.0 mole of the total moles of materials in the uncondensed vapors.

6. The process of claim 4 wherein step (d) is conducted with methylbenzoate as the reflux liquid and in the liquid volume ratio of from 8:1 up to 20:1 of methylbenzoate to water.

7. The process of claim 3 wherein the bed of particles in step (c) comprises palladium disposed on the surface of activated carbon and has a palladium content of from 0.1 up to 1.0 weight percent.

8. The process of claims 5 or 6 wherein the bed of particles in step (c) comprises palladium disposed on the surface of activated carbon and has a palladium content of from 0:1 up to 1.0 weight percent.

* * * * *

UNITED STATES PATENT OFFICE
CERTIFICATE OF CORRECTION

Patent No. 4,215,052                  Dated July 29, 1980

Inventor(s) Hobe Schroeder et al.

It is certified that error appears in the above-identified patent and that said Letters Patent are hereby corrected as shown below:

The Patent Reads:

| Col. | Line | |
|---|---|---|
| 3 | 34 | "components: 2 3 4" and should read --components: 1 2 3 4--. |
| 13 | 18 | "90% benzoic acid" and should read --9.0% benzoic acid-- |

Signed and Sealed this

Fourteenth Day of April 1981

[SEAL]

Attest:

RENE D. TEGTMEYER

Attesting Officer       Acting Commissioner of Patents and Trademarks